United States Patent [19]
Stromgren

[11] 3,945,046
[45] Mar. 23, 1976

[54] FLEXIBLE KNEE SUPPORT
[76] Inventor: Lawrence Thompson Stromgren, 2917 Hillcrest, Hays, Kans. 67601
[22] Filed: Aug. 9, 1974
[21] Appl. No.: 496,158

[52] U.S. Cl............................ 2/22; 2/24; 128/80 C; 128/165
[51] Int. Cl.².......................................... A41D 13/06
[58] Field of Search .......... 128/77, 80 C, 165; 2/16, 2/22, 24

[56] References Cited
UNITED STATES PATENTS

| | | | |
|---|---|---|---|
| 1,587,508 | 6/1926 | Coats | 2/24 |
| 1,622,211 | 3/1927 | Sheehan | 128/80 C |
| 3,463,147 | 8/1969 | Stubbs | 2/24 X |
| 3,506,000 | 4/1970 | Baker | 2/22 |
| 3,581,741 | 6/1971 | Rosman et al. | 128/80 C |

Primary Examiner—Andrew V. Kundrat
Assistant Examiner—Conrad L. Berman
Attorney, Agent, or Firm—D. A. N. Chase

[57] ABSTRACT

A knee support or wrap especially designed for athletes stabilizes the knee ligaments and provides continuous support for the knee regardless of the position of the leg. A tubular, elastic sheath is slipped over the knee, and a pair of elastic straps anchored to the sheath are drawn into place and held by Velcro fasteners. The straps in their operative positions extend in crisscross fashion over the inwardly facing sidewall portion of the sheath, and in directions to duplicate the physiologic stability of the medial knee ligament complex. Felt pads on the sheath under the straps add body to the support, prevent bunching of the elastic sheath, and aid in the distribution of the pressure applied by the elastic straps. The support contains no rigid components and is constructed so as to not impair the normal flexibility of the knee joint.

7 Claims, 7 Drawing Figures

FLEXIBLE KNEE SUPPORT

This invention relates to improvements in knee supports and, in particular, to a support which is capable of stabilizing the knee without impairing normal flexibility so that it may be worn by an athlete without adversely affecting his performance.

Knee braces of various types are in common use at the present time by athletes and others with knee injuries or knees requiring support for some reason. Especially in sports such as football, knee injuries are common and present a constant problem to many athletes. Available braces normally employ either longitudinally extending stays along the sides of the knee or rigid metal strips formed with hinges at the knee joint, either alone or in conjunction with various types of strap arrangements. Oftentimes, these braces are relatively heavy and cumbersome and do not permit normal knee flexibility; thus they are worn only as a matter of necessity.

Furthermore, in football in particular it would be desirable to have a knee support that could be used prophylactically by an athlete to protect the knee joint from the lateral impact that is so common in this sport. The unprotected knee is vulnerable as its weakness is at the inside of the knee joint; therefore, an inwardly directed, lateral impact is particularly dangerous from the standpoint of possible injury.

It is therefore, an important object of the present invention to provide a knee support which is light in weight and not cumbersome and which does not impair the normal flexibility of the knee joint, and yet is effective in stabilizing the knee in use either as a prophylactic device or therapeutically to guard an injured knee.

As a corollary to the foregoing object, it is an important aim of this invention to provide an effective knee support which is devoid of rigid components and is entirely flexible.

Another important object of this invention is to provide a knee support as aforesaid which is constructed in a manner to give continuous support to the knee regardless of the position of the leg.

Still another important object of this invention is to provide a knee support as aforesaid which duplicates the physiologic stability of the medial knee ligament complex in order to impart significantly increased stability to the knee region.

Furthermore, it is an important object of this invention to provide a knee support as aforesaid which may be slipped on the leg of a wearer, rapidly positioned and secured in a minimum of time and with little effort. To this end, it is a further aim of the present invention to provide a support of simple construction devoid of buckles, laces and other such devices.

Figure 1:
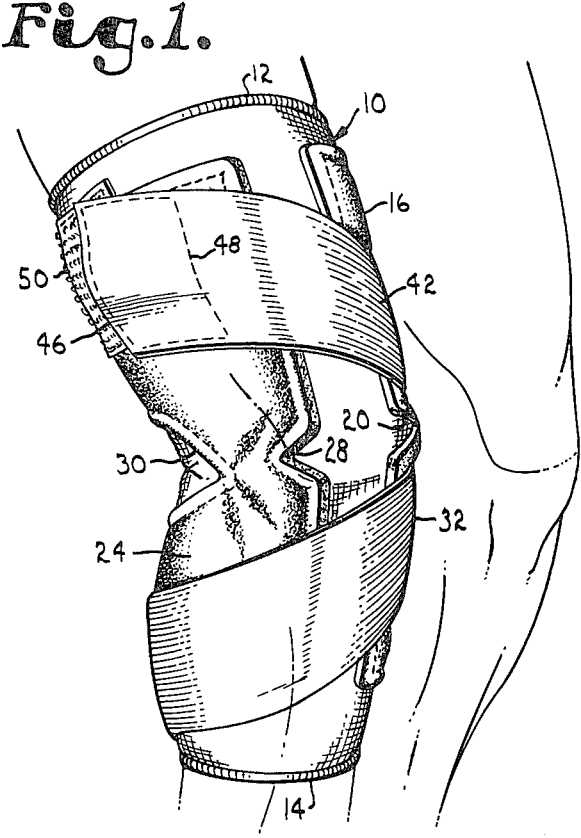
FIG. 1 is a perspective view of the knee support of the present invention, shown on the right knee of the wearer and viewed from the front and outside.
Figure 3:
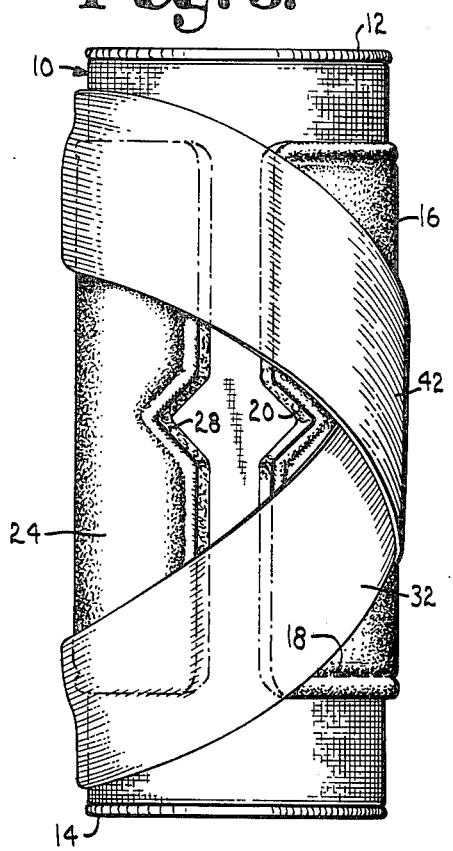
FIG. 3 is a front elevational view of the knee support removed from the wearer.
Figure 4:
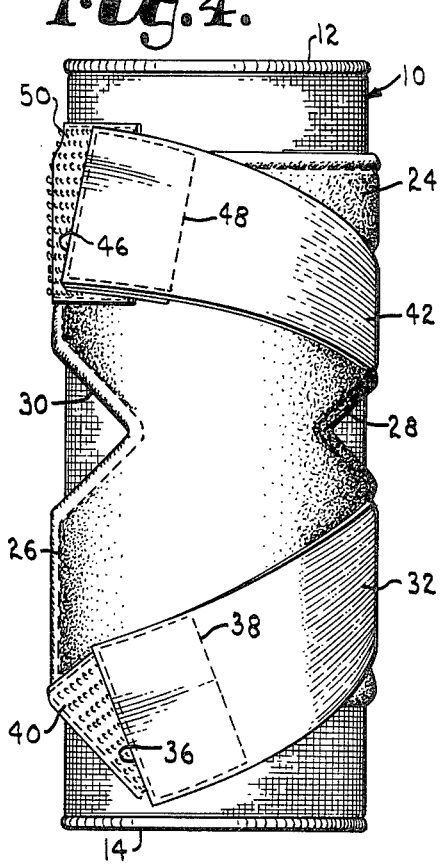
FIG. 4 is an elevational view of the support of FIG. 3, showing the same as seen from the outside of the knee (the right side of the right knee)
Figure 2:
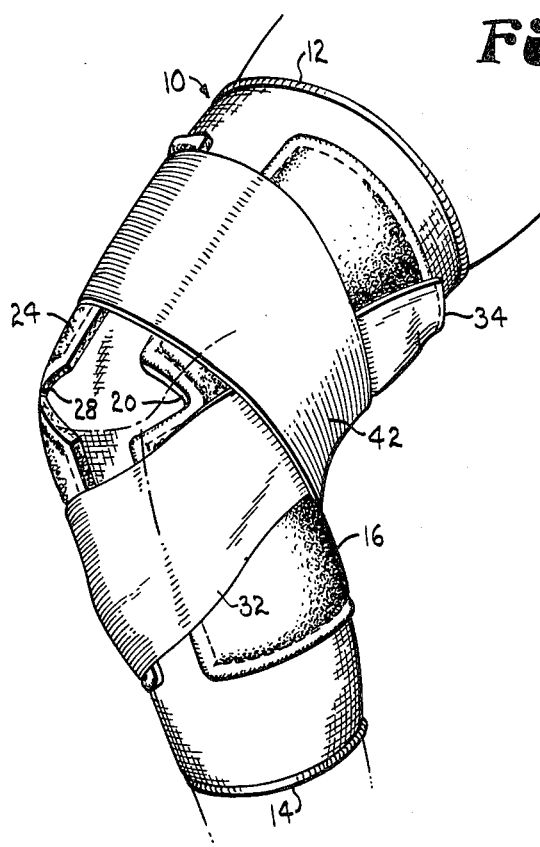
FIG. 2 is a perspective view similar to FIG. 1, showing the knee support as seen from the inside of the knee with the knee joint more fully flexed.

A tubular, elastic sheath broadly denoted 10 receives the leg of the wearer as is clear in FIGS. 1 and 2, and is slipped over the knee to a position where the sheath 10 is approximately longitudinally centered with respect to the knee joint. The knee support of the present invention illustrated herein is for the right knee, it being understood that a similar support could also be worn on the left knee with a reversal of certain components as will be explained. The sheath 10 is an elastic fabric which is stretchable in radial directions but not longitudinally. The sheath is sized to have an unstretched diameter somewhat less than the wearer's leg so that the fabric is stetched as it is pulled over the knee into position. This holds the sheath 10 in place and also imparts some support to the knee region.

The sheath 10 has an upper end 12 and a lower end 14 shown as having a circular configuration in FIGS. 3–7. Therefore, the sheath 10 appears as a cylinder in FIGS. 3–7 as if in place on a cylindrical form. Accordingly, it is to be understood that FIGS. 3–7 are idealized views and that, due to the flexible and elastic nature of the sheath fabric, it will in practice conform to the shape of the leg as illustrated in FIGS. 1 and 2. The upper and lower ends 12 and 14 preferably terminate in sewed edges each containing an elastic band.

A felt pad 16 of generally rectangular configuration is secured to the inside sidewall portion of the tubular sleeve 10 by a continuous line of stitching 18, and has a pair of opposed, front and rear darts 20 and 22 respectively centrally located at its longitudinal edges. A second felt pad 24 of like configuration is secured to the outside sidewall portion of sheath 10 by a continuous line of stitching 26, and has opposed, front and rear darts 28 and 30 respectively aligned with the darts 20 and 22. The dart 30 is somewhat larger to relieve the pad 24 at the rear of the knee joint on the outside of the leg.

Figure 6:
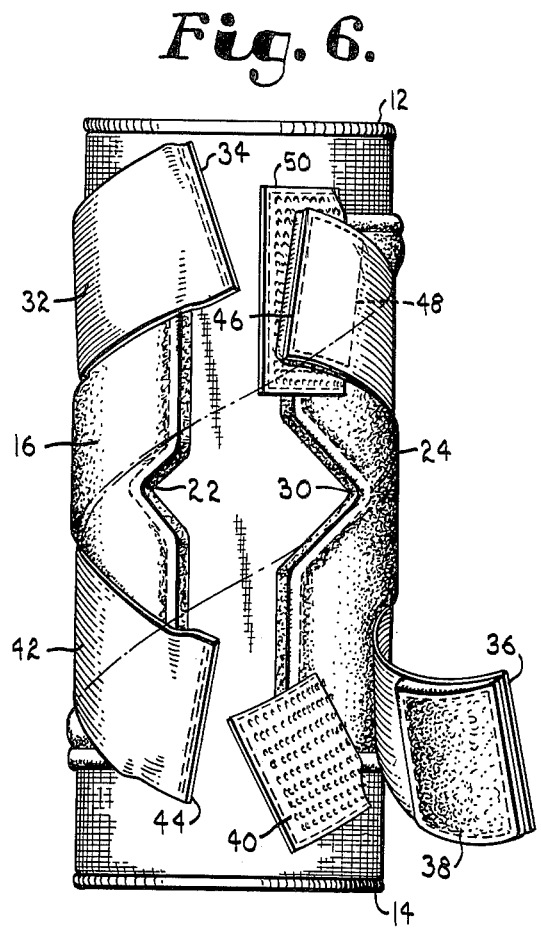
FIG. 6 is a rear elevational view of the support.
Figure 7:
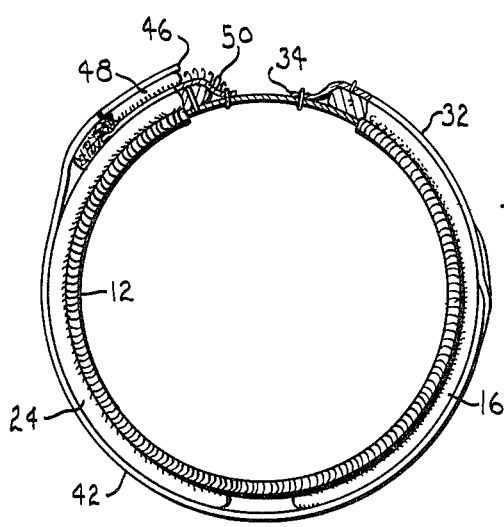
FIG. 7 is a plan view of the support on an enlarged scale with a portion broken away for clarity.

An elastic strap 32 has one of its ends 34 anchored by stitching to the fabric of the sheath 10 at the rear thereof adjacent the upper end 12 (FIG. 6). The opposite end 36 of the strap 32 is provided with a fastener 38 which is adapted to mate with a second fastener 40 sewed on the sheath 10 at the rear thereof adjacent the lower end 14. The fasteners 38 and 40 (known commercially as Velcro) comprise strips of fabric having loops on one strip and hooks on a mating strip which intermesh with the loops in response to applied pressure, and then release when a quick yanking force is applied to peel the strips apart. Accordingly, the generally rectangular Velcro pieces 38 and 40 are faced with the hooks and the loops respectively to provide mating fasteners without requiring snaps, buckles or similar metallic devices.

A second elastic strap 42 has one of its ends 44 anchored by stitching to the fabric of the sheath 10 at the rear thereof adjacent the lower end 14, the opposite end 46 thereof being provided with a fastener 48 adapted to mate with a second fastener 50 sewed on the sheath 10 at the rear thereof adjacent the upper end 12. The fasteners 48 and 50 are fabric fasteners of the Velcro type, the same as the fasteners 38 and 40 discussed above with respect to the strap 32. It should be understood that each of the straps 32 and 42 is longitudinally stretchable and is shorter in length when unstretched than the distance around the sheath 10 from the anchored end of the strap to the corresponding fastener on the sheath. For example, an unstretched length of each strap of approximately two-thirds the length when stretched and secured in place by the fasteners is suitable; this causes the straps to be placed in tension as they are drawn into their operative positions illustrated. Strips of three-inch wide elastic wrap are preferred for the strap material.

A support for the left knee is not illustrated since the same principles apply. The construction is identical except for the obvious reversal of components.

In utilizing the support of the present invention, the sheath 10 is pulled on the leg up over the knee to the position illustrated where it may be appreciated that the kneecap is centered with respect to the sheath and aligned with the darts 20 and 28. The sheath should be approximately 13 to 14 inches in length so as to completely cover the medial knee ligament complex. Once properly located, the straps 32 and 42 are drawn into position and the fasteners 38 and 48 are mated with the fasteners 40 and 50 respectively. The somewhat radially stretched condition of the sheath 10 maintains the device securely in place on the knee and, in itself, gives the knee some support. The pads 16 and 24 add a body sufficient to impart additional stability to the knee and minimize any bunching tendency of the sheath 10. Furthermore, the pads (particularly the pad 16 on the inside of the knee) assist in distributing the pressure applied by the tensioned straps 32 and 42.

Figure 5:
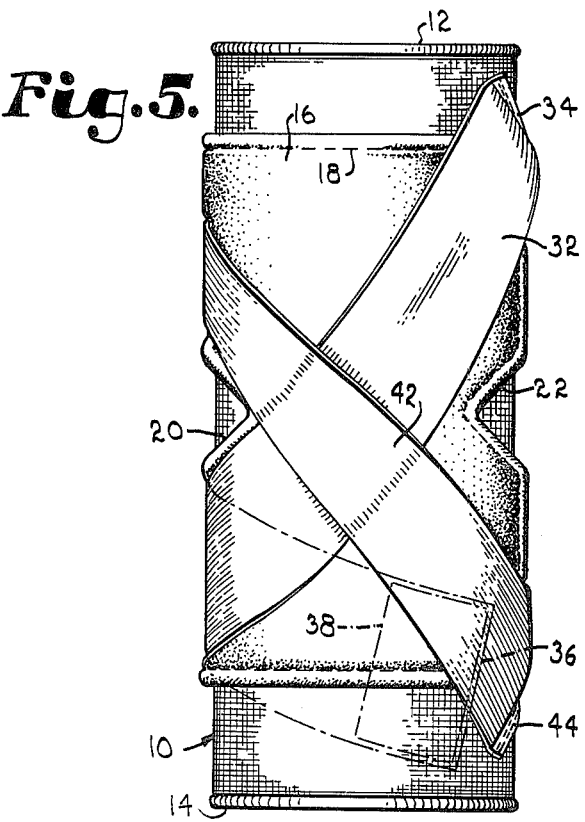
FIG. 5 is an elevational view showing the support as seen from the inside of the knee (the left side of the right knee)

As is particularly clear in FIGS. 2 and 5, the straps 32 and 42 cross on the inside sidewall portion of the sheath 10, the strap 32 then passing under the knee while the strap 42 passes over the knee. Viewing FIG. 4, the straps 32 and 42 diverge on the outside sidewall portion of the sheath 10 as they extend to the corresponding fasteners 40 and 50. Accordingly, the straps follow the direction of the anatomic fibers of the knee ligaments and apply laterally outwardly directed pressure to the knee region from the inside of the leg. As may be seen most clearly in FIG. 6, proper positioning of the anchored ends 34 and 44 of the straps 32 and 42 and the corresponding fasteners 40 and 50 on the sheath 10 is important so that the straps, when drawn into place, will be caused to assume the crisscross configuration at the inside of the knee.

Being located as discussed above and relatively wide, the elastic straps 32 and 34 considerably reduce the tendency of medial knee ligament instability and/or any external tibial rotary instability. The rotary instability refers to the action of the foot in swinging in one direction without a corresponding movement of the knee, thereby causing a twist. Reduction of these two types of instability is attributed in the present invention to the duplication of the physiologic stability of the medial knee ligament complex through the particular strap positions discussed above that enable the straps to follow and support the natural ligaments.

Furthermore, the arrangement of the present invention gives continuous support to the knee regardless of the position of the leg as may be seen, for example, by a comparison of FIGS. 1 and 2. Being completely flexible with no rigid components, there is no significant reduction in the normal flexibility of the knee joint. This is particularly important in athletics where the athlete, though wishing support, does not desire to be impeded either in speed or maneuverability. This feature of the present invention, together with its light weight and ease of installation and removal, make it particularly useful as a prophylactic device since the athlete's efficiency is not compromised.

Having thus described the invention, what is claimed as new and desired to be secured by Letters Patent is:

1. A knee support comprising:
   a tubular, elastic sheath adapted to receive the leg of a wearer and to be positioned over the knee,
   said sheath being of a length sufficient to cover the medial knee ligament complex when the sheath is positioned over the knee,
   said sheath having upper and lower ends and opposed, inwardly and outwardly facing sidewall portions;
   first and second elastic straps each having opposed ends;
   means anchoring one end of said first strap to said sheath adjacent the upper end thereof, and anchoring one end of said second strap to said sheath adjacent the lower end thereof; and
   mating fasteners on the opposite ends of said straps and said sheath, said fasteners on the sheath being located adjacent said upper and lower ends of the sheath and mating with the fasteners on said second and first straps respectively,
   said straps being drawn around the sheath into operative positions crossing each other on the inwardly facing sidewall portion of the sheath upon engagement of the mating fasteners and, in said positions, said first and second straps being adapted to pass under and over the knee respectively, whereby to stabilize the knee without impairing normal flexibility.

2. The knee support as claimed in claim 1, wherein said anchoring means and said fasteners on the sheath are located at the rear of the sheath, and wherein said straps diverge on the outwardly facing sidewall portion of the sheath as they extend therearound to the fasteners on the sheath.

3. The knee support as claimed in claim 2, wherein each of said straps is longitudinally stretchable and is shorter in length when unstretched than the distance from said one anchored end thereof to the corresponding fastener on the sheath.

4. The knee support as claimed in claim 3, wherein a pad is provided on said inwardly facing sidewall portion of the sheath over which said straps are streched in their operative positions.

5. The knee support as claimed in claim 1, wherein said straps are longitudinally stretchable and are in tension in their operative positions.

6. The knee support as claimed in claim 5, wherein a pad is provided on said inwardly facing sidewall portion of the sheath over which said straps are stretched in their operative positions.

7. The knee support as claimed in claim 6, wherein a second pad is provided on the outwardly facing sidewall portion of said sheath, said pads having front and rear darts adapted to be aligned with the knee.

* * * * *